United States Patent [19]

Acton et al.

[11] 3,952,114

[45] Apr. 20, 1976

[54] 1,4-CYCLOHEXADIENE-1-CARBOXALDEHYDE SYN-OXIME SYNTHETIC SWEETENING AGENTS

[75] Inventors: Edward M. Acton; Michael W. Lerom; Herbert Stone, all of Menlo Park, Calif.

[73] Assignee: Stanford Research Institute, Menlo Park, Calif.

[22] Filed: Aug. 25, 1975

[21] Appl. No.: 607,266

Related U.S. Application Data

[63] Continuation of Ser. No. 477,995, June 10, 1974, Pat. No. 3,919,318.

[52] U.S. Cl................................ 426/548; 260/566 A
[51] Int. Cl.$^2$.......................................... A23L 1/236
[58] Field of Search.................. 426/548; 260/566 A

[56] References Cited
UNITED STATES PATENTS

| | | | |
|---|---|---|---|
| 3,699,132 | 10/1972 | Acton et al. | 426/548 X |
| 3,780,194 | 12/1973 | Acton et al. | 426/548 |
| 3,833,654 | 9/1974 | Acton et al. | 426/548 X |

OTHER PUBLICATIONS

Acton et al., *J. Agr. Food Chem.*, Vol. 18, No. 6 (1970), pp. 1061–1068.

*Primary Examiner*—A. Louis Monacell
*Assistant Examiner*—Esther L. Massung
*Attorney, Agent, or Firm*—Donovan J. De Witt

[57] ABSTRACT

New compounds 4-methyl-1,4-cyclohexadiene-1-carboxaldehyde syn-oxime, 4-methoxymethyl-1,4-cyclohexadiene-1-carboxaldehyde syn-oxime, and 4-(1-methoxyethyl)-1,4-cyclohexadiene-1-carboxaldehyde syn-oxime, as well as the compound 1,4-cyclohexadiene-1-carboxaldehyde syn-oxime, are found to have a high degree of sweetness which is accompanied by very little off-taste. The compounds have good stability even in acid solution. They give no evidence of toxicity and can be employed in foods and beverages as synthetic sweetening ingredients.

3 Claims, No Drawings

1,4-CYCLOHEXADIENE-1-CARBOXALDEHYDE SYN-OXIME SYNTHETIC SWEETENING AGENTS

This is a continuation of application Ser. No. 477,995, filed June 10, 1974, now U.S. Pat. No. 3,919,318.

BACKGROUND OF INVENTION

In appraising the utility of synthetic sweetening agents, several important factors must be kept in mind. Thus, of the total taste characteristics of the product, it is essential that a high proportion represent sweetness qualities which are accompanied by as small as possible a proportion of off-tastes. More particularly, the sweet taste factor should be at least 70%, and preferably at least 80% of the total taste characteristics. Further, the compound should manifest good stability, particularly under the acid conditions which characterize various carbonated beverages. Preferably the compound should also have good water solubility so that concentrates can be employed in formulating various comestible products. It is the object of this invention to provide sweetening compounds which meet these various quality characteristics.

DISCUSSION OF PRIOR ART

Related oxime sweetener compounds are disclosed in U.S. Pat. No. 3,780,194, to Acton et al., issued Dec. 18, 1973. The compounds thereof do not possess the 1,4-cyclohexadiene moiety which characterizes the compounds of the present invention, and their "sweetness" characteristics are undesirably low. The related oxime sweetener compound disclosed in U.S. Pat. No. 3,699,132, to Acton et al., issued Oct. 17, 1972, does not contain the 1,4-cyclohexadiene moiety, the principal disadvantage of the compound being a lack of stability under the acid conditions found in carbonated beverages. Allowed application, Ser. No. 360,844 of Acton et al., filed May 16, 1973, discloses related oxime sweetener compounds, but having a cyclohexene nucleus. The sweetness characteristics of these compounds are well below those of the compounds disclosed herein. The paper entitled "Structure-Taste Relationships in Oximes Related to Perillartine" by Acton et al., *J. Agric. and Food Chem.*, 18, 1061–1068, Nov.–Dec. (1970), discloses, inter alia, a single 1,4-cyclohexadiene based oxime (compound number 5 in the paper) which had not been isolated at the time the paper was written. This compound, designated 4-isopropyl-1,4-cyclohexadiene-1-carboxaldehyde syn-oxime, has recently been prepared in pure form. It is found to have poor sweetness qualities (only 34 percent of the total taste characteristics) along with a high level (40%) of tastes identified as "bitter". Further, the solubility of this compound in aqueous solution is so low that the total taste intensity of a saturated solution is only 45% of that of an 8.55% aqueous sucrose solution employed as control.

Frank et al., *J. Amer. Chem. Soc.*, 71, 3889 (1949), disclose phellandral syn-oxime, a compound which incorporates a cyclohexene nucleus and is described by the authors as being "not sweet". We have prepared this compound and find it to be substantially insoluble in water, with no appreciable taste qualities at all.

Unterhalt et al., *Zeitschrift für Lebensmittel-Untersuchung und Forschung*, 147, 153 (1971), disclose a number of oximes, three of which are described as being sweet. Of the latter compounds, one incorporates a phenyl nucleus, with the carbon atom para to the carboxaldehyde syn-oxime group being substituted by a methoxy group. We have found this compound to have a sweetness factor of but 15%. The other two compounds described as sweet form the subject of the above-identified Acton et al. U.S. Pat. No. 3,780,194 and have relatively low sweetness levels of approximately 50%.

Eichengrum Eichengrün al., *Berichte*, 23, 2885 (1890); Beilstein, 7, 147, disclose an oxime wherein the carboxaldehyde syn-oxime group is attached to an otherwise unsubstituted 1,3-cyclohexadiene nucleus. The authors describe this compound as being "unpleasantly sweet". We have found it to have a relatively low sweetness factor of 50%.

Birch et al., *Australian J. Chem.*, 7, 256 (1954) disclose 1,4-cyclohexadiene oxime-1-carboxaldehyde syn-oxime, the sweetener utility of which forms a subject of the present invention. The authors gave no information about the taste of this compound.

SUMMARY OF INVENTION

The present invention rests in part on the discovery of the novel 1,4-cyclohexadiene-1-carboxaldehyde syn-oxime compounds which are substituted in the 4 position by a methyl, methoxymethyl, or 1-methoxyethyl group. The invention also rests on the discovery that these substituted oxime compounds, and (to a somewhat lesser extent) the corresponding unsubstituted oxime compound as well, have outstandingly good sweet taste qualities which are accompanied by but minor off-tastes. For each of these compounds the percentage of total taste characteristics identified as sweet is at least 70%, this percentage rising to a level above 80% in the case of the novel substituted oxime compounds hereof. All four compounds have good stability in aqueous solution even under strongly acid conditions, and, with the exception of the methyl substituted oxime, they also have good water solubility.

The unsubstituted (known) oxime compound referred to above is designated herein by the reference (I) and its preparation is described in Example 1.

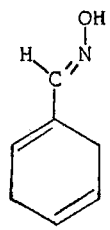

I

The novel oximes of this invention have the structure

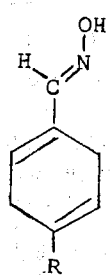

wherein R represents a methyl, methoxymethyl, or 1-methoxyethyl group.

The methyl-substituted oxime compound is designated herein by the reference (II), and its preparation is described in Example 2.

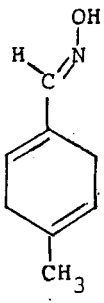

II

The methoxymethyl-substituted oxime compound is designated herein by the reference (III), and its preparation is described in Example 3.

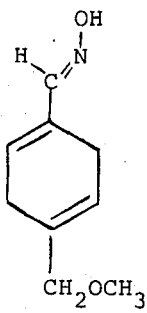

III

The 1-methoxyethyl-substituted oxime compound is designated herein by the reference (IV) and its preparation is described in Example 4.

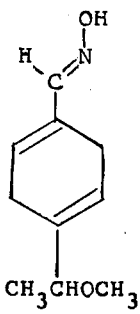

IV

The following examples describe the preparation of compounds (I), (II), (III), and (IV), the synthesis employed in each case proceeding via the designated intermediates which are underscored.

EXAMPLE 1

1,4-Cyclohexadiene-1-carboxaldehyde syn-oxime (R = H)

1,3-Dimethyl-2-phenylimidazolidine.

Using the method of Birch and Dastur, Austral. J. Chem., 26, 1364 (1973), a solution of 5.5 g of benzaldehyde in 25 ml of benzene was added dropwise to a stirred solution of sym-dimethylethylenediamine in 15 ml of benzene, and heated at 60° for 2 hrs. Evaporation and distillation at 55° (0.35 mm) afforded 6.4 g, identified by nmr.

1,3-Dimethyl-2-(1,4-cyclohexadienyl)imidazolidine.

Using the methods of Birch et al., Austral. J. Chem. 7, 256 (1954) and 26, 1363 (1973), a solution of the above product in 25 ml of dry tetrahydrofuran and 32 ml of t-butanol was added to 300 ml of liquid ammonia. To the stirred solution under $N_2$ was added 3.0 g of lithium wire in 1-cm pieces during 15 minutes. Stirring was continued for 2 hr, and ammonium chloride was added cautiously in portions to discharge the unused lithium. The ammonia was allowed to evaporate, water was added to the residue and the product was extracted with dichloromethane. The extracts, dried and evaporated, yielded 8.5 g of liquid, identified by nmr, which disclosed the presence of 1,3-dimethyl-2-(1-cyclohexenyl)imidazolidine as contaminant.

1,4-Cyclohexadiene-1-carboxaldehyde.

The above product was stirred in 150 ml of 1M hydrochloric acid for 1 hr, and the liberated aldehyde was extracted with dichloromethane. The extracts, dried and evaporated, afforded 4.1 g, identified by ir and nmr spectra. [This aldehyde was previously described by Birch et al., Austral. J. Chem., 7, 256 (1954) and by Petrov, Zhur. Obshchei Khim., 24, 2136 (1954).]

1,4-Cyclohexadiene-1-carboxaldehyde syn-oxime.

A solution of the above aldehyde, 2.75 g of hydroxylamine hydrochloride, and 3.33 g of sodium bicarbonate in 100 ml of 1:1 ethanol-water was refluxed for 1 hr, cooled, diluted with water, and extracted with dichloromethane to yield 4.3 g of crude oxime as a crystalline residue upon evaporation. Fractional crystallization from hexane, and finally from aqueous ethanol, separated the contaminating cyclohexene-1-carboxaldehyde syn-oxime and yielded 0.15 g of pure product, mp 103.5°–104.0°, identified by nmr.

Analysis: Calculated for $C_7H_9NO$: C, 68.3; H, 7.37; N, 11.4. Found: C, 68,0; H, 7.34; N, 11.3.

[This oxime has been described by Birch et al., Austral. J. Chem., 7, 256 (1954), who report mp 97°–98° and give an unacceptable analysis (found C, 69.0).]

EXAMPLE 2

4-Methyl-1,4-cyclohexadiene-1-carboxaldehyde syn-oxime (R = $CH_3$)

1,3-Dimethyl-2-(p-tolyl)imidazolidine.

Using the method of Birch and Dastur, Austral. J. Chem., 26, 1364 (1973), a solution of 48 g of p-tolualdehyde in 185 ml of benzene was added dropwise to a stirred solution of 25 g of sym-dimethylethylenediamine in 95 ml of benzene, and heated at 60° for 2 hrs. Evaporation and distillation at 52° (0.1 mm) afforded 48 g, identified by nmr.

1,3-Dimethyl-2-(4-methyl-1,4-cyclohexadienyl)imidazolidine.

A 10-gram portion of the above product, still using the method of Birch, in 40 ml of dry tetrahydrofuran and 50 ml of t-butanol was added to 500 ml of liquid ammonia under nitrogen, and 4.9 g of lithium wire in 1-cm pieces was added with stirring. Processing as in Example 1 afforded 10 g of pure liquid, identified by nmr.

4-Methyl-1,4-cyclohexadiene-1-carboxaldehyde.

The above product was treated with 150 ml of 2M hydrochloric acid. Processing as in Example 1 afforded 6.7 g of aldehyde, identified by nmr. [This aldehyde was previously described by Petrov, Zhur. Obshchei Khim., 25, 517 (1955).]

4-Methyl-1,4-cyclohexadiene-1-carboxaldehyde syn-oxime.

The above aldehyde was treated with 4.3 g of hydroxylamine hydrochloride and 5.2 g of sodium bicarbonate in 90 ml of 1:1 ethanol-water, refluxed for 1 hr, and processed as in Example 1. Recrystallization from hexane-chloroform and then from aqueous ethanol afforded 4.3 g of pure oxime, mp 107.0°–107.5°, identified by nmr.

Analysis: Calculated for $C_8H_{11}NO$: C, 70.0; H, 8.08; N, 10.2. Found: C, 69.8; H, 8.30; N, 10.1.

EXAMPLE 3

4-Methoxymethyl-1,4-cyclohexadiene-1-carboxaldehyde syn-oxime ($R = CH_2OCH_3$).

4-Hydroxymethyl-1-methoxy-1,4-cyclohexadiene.

Using the method of Birch, J. Proc. Roy. Soc. New South Wales, 83, 245 (1949), 27.6 g of 4-methoxybenzyl alcohol in 93 ml of dry ethanol was added to 600 ml of liquid ammonia and reduced with 23 g of sodium added in pieces. After 2 hrs stirring, the excess sodium was discharged by cautiously adding 60 g of ammonium chloride. The ammonia was allowed to evaporate, water was added to the residue, and the product was extracted with dichloromethane. The extracts, dried and evaporated, afforded 12.1 g, bp 72°–74° (0.1 mm), identified by nmr.

4-Methoxymethyl-1-methoxy-1,4-cyclohexadiene.

Using the method of Botica and Mirrington, Austral. J. Chem. 24, 1467 (1971), the above alcohol in 90 ml of dry ether was converted to the alkoxide by adding the solution to a stirred suspension of 58% sodium hydride (mineral oil dispersion) in 55 ml of dry 1,2-dimethoxyethane. Stirring was continued for 1 hr, and the alkoxide suspension was then cooled to 10° and treated with 7.1 ml of methyl iodide in 20 ml of ether. Stirring was continued overnight at room temperature, the mixture was poured onto 300 ml of ice and water, and the product was extracted with ether. Evaporation of the dried extracts yielded 18.5 g of liquid (still containing solvent), identified by nmr spectrum.

4-Methyoxymethyl-3-cyclohexen-1-one.

In a modification of the procedure of Wilds and Nelson, J. Amer. Chem. Soc., 75, 5366 (1953), a stirred solution of the above product in 260 ml of methanol was treated dropwise with a solution of 2.52 g of oxalic acid dihydrate in 140 ml of water. Stirring was continued for 1 hr, 500 ml of water was added, and the product was extracted with dichloromethane. The extracts were washed with water and with sodium bicarbonate solution, dried, and evaporated to yield 17.3 g of liquid, identified by ir and mnr.

4-Methoxymethyl-1-cyano-1,4-cyclohexadiene.

Using the method of Wheeler and Lerner, J. Amer. Chem. Soc., 78, 63 (1956), also described in U.S. patent application, Ser. No. 360,844, filed May 16, 1973, the above ketone was treated dropwise, with stirring at 0°–10°, with 11.7 g of potassium cyanide in 40 ml of water and 17.9 g of sodium bisulfite in 40 ml of water. Stirring was continued for 1.5 hr at 0°–10° and 1.5 hr at room temperature, and the cyanohydrin was extracted with ether. The extracts were washed with water, dried, and evaporated to yield 15.8 g of oil, identified by ir. This cyanohydrin in 20 ml of benzene and 20 ml of pyridine was treated dropwise, with ice-bath cooling, with a solution of 23.6 ml of phosphoryl chloride in 24 ml of pyridine. The mixture was refluxed for 15 min, cooled, diluted with 100 ml of benzene, and poured on 300 g of crushed ice. The benzene layer was separated, the aqueous layer was extracted with benzene, and the combined benzene solutions were washed with 1M hydrochloric acid and with water, dried, and evaporated to yield 13 g of liquid, identified by ir and nmr, which disclosed the presence of the 1,3-diene isomer as contaminant.

4-Methoxymethyl-1,4-cyclohexadiene-1-carboxaldehyde.

By the method described in our patent, U.S. Pat. No. 3,780,194, and in U.S. patent application Ser. No. 360,844, filed May 16, 1973, the above nitrile in 75 ml of dry benzene was treated dropwise, with stirring and ice cooling, with 65 ml of a 25% solution of diisobutylaluminum hydride in benzene. After 2 hrs stirring at 20°, the solution was poured onto a mixture of 120 ml of 12M hydrochloric acid and 580 g of crushed ice. The mixture was heated to 40° for 10 min, cooled to room temperature, and the aldehyde was extracted with ether. The extracts were washed with water, aqueous sodium bicarbonate solution, water, and were dried and evaporated at 30° (25 mm) to yield 8.3 g of liquid, identified by ir and nmr, which disclosed the presence of the 1,3-diene isomer as contaminant.

4-Methoxymethyl-1,4-cyclohexadiene-1-carboxaldehyde syn-oxime.

The above aldehyde, 6.6. g of hydroxylamine, and 8.0 g of sodium bicarbonate in 60 ml of ethanol and 30 ml of water was processed as in Example 1. The crude oxime was separated from the contaminating 1,3-isomer by fractional recrystallization from hexane and, finally, from aqueous ethanol. The pure oxime melted at 91.0°–91.5°, and was identified by nmr.

Analysis: Calculated for $C_9H_{13}NO_2$: C, 64.6; H, 7.83; N, 8.38. Found: C, 64.9; H, 7.66; N, 8.48.

EXAMPLE 4

4-(1-Methoxyethyl)-1,4-cyclohexadiene-1-carboxaldehyde syn-oxime ($R = CH_3CHOCH_3$).

(Methods and procedures were the same as for the corresponding conversions in Example 3.)

4-(1-Hydroxyethyl)-1-methoxy-1,4-cyclohexadiene.

A solution of 40 g of 2-(4-methoxyphenyl)ethanol in 80 ml of ethanol and 800 ml of ammonia reduced with 30.4 g of sodium to yield 27.4 g, bp 87°–89° (0.7 mm), identified by nmr.

4-(1-Methoxyethyl)-1-methoxy-1,4-cyclohexadiene.

The above product in 110 ml of ether was converted to the alkoxide with 14.7 g of 58% sodium hydride and O-methylated with 14.8 ml of methyl iodide to yield 24.9 g, bp 43°–45° (0.1 mm), identified by nmr, which disclosed contamination by 14% of the benzene analog 4-(1-Methoxyethyl)-3-cyclohexen-1-one.

The above product was hydrolyzed with 4.0 g o oxalic acid dihydrate in 400 ml of methanol and 200 m of water to yield 23.3 g of ketone, identified by ir.

4-(1-Methoxyethyl)-1-cyano-1,4-cyclohexadiene.

The above ketone was treated with 20.4 g of potas sium cyanide and 31.2 g of sodium bisulfite in 130 ml o water to yield 26.5 g of the cyanohydrin, identified b; ir. It was dehydrated with 41 ml of phosphoryl chlorid in 75 ml of pyridine solution to give 18.9 g, identifie by ir and nmr, which disclosed the presence of th 1,3-isomer as contaminant.

4-(1-Methoxyethyl)-1,4-cyclohexadiene-1-carboxaldehyde.

The above nitrile in 100 ml of benzene was reduced with 87 ml of a 25% solution of diisobutylaluminum hydride in benzene to yield 10.6 g of aldehyde, identified by ir and nmr, which disclosed presence of the 1,3-isomer as contaminant.

4-(1-Methoxyethyl)-1,4-cyclohexadiene-1-carboxaldehyde syn-oxime.

Without purification, the above aldehyde was treated with 4.86 g of hydroxylamine hydrochloride and 5.88 g of sodium bicarbonate in 25 ml of water and 50 ml of ethanol. The crude oxime mixture was subjected to column chromatography on silica gel, whereupon elution with hexane-chloroform (1:1) separated the aromatic impurities. Chloroform elution then afforded the product oxime in a 3:2 mixture with the isomeric 1,3-cyclohexadiene. This mixture was resolved by trituration with pentane to remove gummy or colored material, vacuum sublimation of the residual white solid, and fractional crystallization of the sublimate from hexane. (Much of the 1,3-isomer seemed to polymerize during the process, and was left in the gummy residues.) A final recrystallization from aqueous ethanol afforded the pure product, mp 108° with sublimation, identified by nmr.

Analysis: Calculation for $C_{10}H_{15}NO_2$: C, 66.3; H, 8.34; N, 7.73. Found: C, 66.5; H, 8.39; N, 7.86.

Using tasting panels of five or six experienced people both the intensity of the taste and its quality were evaluated for each of the (I), (II), (III), and (IV) oximes. In the first of these tests, the taste intensity of oxime solutions of varying concentration was evaluated against an 0.25 M (8.55%) sucrose solution taken as the standard of unit intensity. In this fashion the concentration of each oxime compound having essentially the same taste intensity of that of the sugar was determined. This concentration worked out to be 0.0012 M (0.015%) for (I), 0.0005 M (0.007%) for (II), 0.001 M (0.017%) for (III) and 0.0008 M (0.014%) for (IV). Thereafter, using solutions of each oxime having intensity levels between about 0.4 and 1.5 or 2.0, the panel members estimated the percent of the taste quality which was identifiable as sweet, as well as the percentage of off-taste characteristics was identified as bitter, "other", etc.

Table 5 given below presents information as to the melting point, optical isomerism and solubility of the various oximes, together with data derived from the findings of the tasting panels.

Table 5

| PHYSICAL AND TASTE CHARACTERISTICS OF OXIME COMPOUNDS (I) – (IV) | | | |
|---|---|---|---|
| (I) | (II) | (III) | (IV) |
| Melting point: | | | |
| 103.5–104.0° | 106.5–107.0° | 91.0–91.5° | 108° sublimes |
| Optical isomerism: | | | |
| none | none | none | dl pair |
| Concentration of saturated solution: | | | |
| 0.19% | 0.008% | 0.34% | 0.07% |
| 0.015 M | 0.0006 M | 0.02 M | 0.0039 M |
| Total taste intensity of saturated solution (compared to 0.25 M sucrose as 1): | | | |
| (~12)[a] | 1.3 | (~18)[a] | (~5)[a] |
| Taste intensity of oxime compared to sucrose: | | | |
| molar basis 200x | 500x | 225x | 300x |
| weight basis 560x | 1250x | 460x | 570x |
| Taste characteristics (% of total taste): | | | |
| sweet 70 | 83 | 89 | 94 |
| bitter 3 | 2 | 2 | 1 |
| menthol / coconut / licorice 9 | 11 | 4[b] | 2 |

[a]Extrapolated from values at lower concentrations near unit intensity
[b]Some fruit, berry off-tastes

We claim:

1. The compound which is 4-methyl-1,4-cyclohexadiene-1-carboxaldehyde syn-oxime.

2. The method of sweetening a comestible which comprises adding 1,4-cyclohexadiene-1-carboxaldehyde syn-oxime, 4-methyl-1,4-cyclohexadiene-1-carboxaldehyde syn-oxime, 4-methoxymethyl-1,4-cyclohexadiene-1-carboxaldehyde syn-oxime, or 4-(1-methoxyethyl)-1,4cyclohexadiene-1-carboxaldehyde syn-oxime.

3. The method of claim 2 wherein the comestible is also sweetened with sucrose.

* * * * *